US006833467B2

(12) United States Patent
Ma et al.

(10) Patent No.: US 6,833,467 B2
(45) Date of Patent: Dec. 21, 2004

(54) METHOD FOR PREPARING PENTAERYTHRITOL PHOSPHATE ALCOHOL BY MECHANOCHEMICAL SYNTHESIS

(75) Inventors: Chong Ma, Tao-Yuan (TW); Wen-Yo Chen, Tao-Yuan (TW); Yuen-Hsin Peng, Tao-Yuan (TW)

(73) Assignee: Chung-Shan Institute of Science & Technology, Tao-Yuan (TW)

( * ) Notice: Subject to any disclaimer, the term of this patent is extended or adjusted under 35 U.S.C. 154(b) by 240 days.

(21) Appl. No.: 10/291,389

(22) Filed: Nov. 12, 2002

(65) Prior Publication Data

US 2004/0092760 A1 May 13, 2004

(51) Int. Cl.$^7$ .............................................. C07F 9/6571
(52) U.S. Cl. ....................................................... 558/74
(58) Field of Search ............................................ 558/74

(56) References Cited

U.S. PATENT DOCUMENTS

| 4,454,064 | A | * | 6/1984 | Halpern et al. ................ 558/74 |
| 5,237,085 | A | * | 8/1993 | Telschow et al. ............. 558/74 |
| 6,455,722 | B1 | * | 9/2002 | Vyverberg et al. ............ 558/74 |
| 6,737,526 | B1 | * | 5/2004 | Ma et al. ..................... 544/195 |

* cited by examiner

Primary Examiner—Johann Richter
Assistant Examiner—Ebenezer Sackey
(74) Attorney, Agent, or Firm—Bacon & Thomas, PLLC

(57) ABSTRACT

Mechanochemical synthesis of pentaerythritol phosphate alcohol is disclosed. The synthesis is carried out by ball milling a mixture containing $P_2O_5$, pentaerythritol, an alkyl benzene having one or two C1–C5 alkyl groups, and a metal halide catalyst, in a ball mill as a reactor and at a temperature of 70–150° C.

8 Claims, No Drawings

METHOD FOR PREPARING PENTAERYTHRITOL PHOSPHATE ALCOHOL BY MECHANOCHEMICAL SYNTHESIS

BACKGROUND OF THE INVENTION

U.S. Pat. No. 4,454,064 discloses a method for preparing pentaerythritol phosphate alcohol, which comprises reacting pentaerythritol and $POCl_3$ in dioxane solvent at 75–125° C. The pentaerythritol phosphate alcohol prepared is an intermediate that can be used to synthesize PU flame retardants and plasticizers. HCl gas is also generated in this method, and a large amount of water is required to wash away HCl from the product mixture. Moreover, an excessive amount of $POCl_3$ is used in this method, which results in a residue solution containing unreacted $POCl_3$.

U.S. Pat. No. 4,478,998 (1984) discloses a method for synthesizing amino-s-triazine salt of a phosphoric acid from pentaerythritol phosphate alcohol. The amino salt synthesized can be used as a flame retardant additive for special polymeric compositions.

SUMMARY OF THE INVENTION

The present invention provides a waste-reduction process for producing pentaerythritol phosphate alcohol. The features of the process of the present invention are as follows:

1. The process uses $P_2O_5$ as a reactant.
2. The process uses a mechanochemical synthesis method and uses a ball mill as a reactor.
3. The process uses an alkyl benzene, such as toluene or xylene, as a solvent. The alkyl benzene may have one or two identical or different alkyls having 1 to 5 carbons.
4. The solvent used in the process is pre-heated to 70–150° C.
5. The process uses metal halide $MX_2$, such as $MgCl_2$ etc., as a catalyst, wherein M=Mg, Zn, or Al; and X=Cl, or Br. The weight ratio of the catalyst to pentaerythritol is 1:99 to 5:95.

Compared to the conventional process, a waste-reduction process for producing pentaerythritol phosphate alcohol according to the present invention has the following three advantages: (a) no generation of waste gas of HCl; (b) free of a waste aqueous solution generated from neutralization of HCl waste gas; and (c) avoiding handling of a residue solution containing unreacted $POCl_3$. Since the present invention uses $P_2O_5$ to replace $POCl_3$, no HCl is generated in the process, and no residue solution containing unreacted $POCl_3$ is formed. Moreover, the solvent used in the present invention (e.g. toluene) can be recycled, thereby achieving an objective of waste reduction.

Pentaerythritol will become a molten state in toluene at 90–100° C. and can react with $P_2O_5$. Since a molten pentaerythritol has a very high viscosity and is difficult to be agitated, the reaction yield is usually not high. Therefore, a mechanochemical synthesis, e.g. a ball mill, is used to achieve an ideal agitatioin such that pentaerythritol and $P_2O_5$ can have a sufficient contact with each other, thereby increasing the yield. The present invention adopts a ball mill process which also achieves the following improvements: increasing the purity, increasing the yield, reducing the particle size, simplifying the process, and without heating/cooling during the reaction.

DETAILED DESCRIPTION OF THE INVENTION

Several factors affecting the synthesis of pentaerythritol phosphate alcohol are discussed in the following:

1. Study on the Reaction Solvent

The molecular structure unit of phosphorus pentoxide is $P_4O_{10}$, usually represented by $P_2O_5$. Phosphorus pentoxide is a very strong dehydration agent, and is liable to react with water to form phosphoric acid.

$P_2O_5+3H_2O \rightarrow 2H_3PO_4$

Furthermore, it can grab $H_2O$ from reactant molecules to form metaphosphoric acid and related inorganic or organic material, e.g.

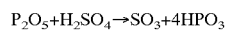
$P_2O_5+H_2SO_4 \rightarrow SO_3+4HPO_3$

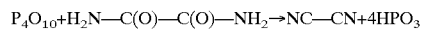
$P_4O_{10}+H_2N-C(O)-C(O)-NH_2 \rightarrow NC-CN+4HPO_3$

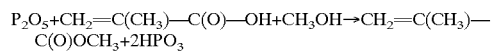
$P_2O_5+CH_2=C(CH_3)-C(O)-OH+CH_3OH \rightarrow CH_2=C(CH_3)-C(O)OCH_3+2HPO_3$ $P_2O_5$ reacts with ethyl ether to form triethyl phosphate:

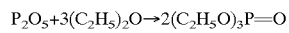
$P_2O_5+3(C_2H_5)_2O \rightarrow 2(C_2H_5O)_3P=O$

The strong reactivity of phosphorus pentoxide makes the selection of the reaction solvent greatly restricted. The inventors of the present invention have tried using a solvent such as n-hexane, diethyl phosphate, and toluene, etc. for performing the reaction, in which the reaction of using n-hexane as a solvent is not ideal and has an extremely low yield. When diethyl phosphate is used as a solvent, the reaction has a very good yield. However, since the properties of diethyl phosphate are too close to the properties of the product pentaerythritol phosphate alcohol, they are difficult to be separated. Therefore, toluene is selected as a reaction solvent.

Pentaerythritol can be dissolved in diethyl phosphate solvent, therefore, after addition of $P_2O_5$, the reaction can take place at a reaction temperature of 90° C. While not dissolving in toluene, pentaerythritol will turn into a molten state when the temperature rises to 90° C. and can react with $P_2O_5$. Since pentaerythritol in its molten state has an extremely high viscosity and is difficult to agitate, the reaction yield is not high. Therefore, how to achieve an ideal agitation for pentaerythritol to have a sufficient contact with $P_2O_5$ is a key factor in increasing the yield. Pentaerythritol does not dissolve at the boiling point of n-hexane at 68° C. and has no change in state at this temperature, this could be a reason why it does not react with $P_2O_5$ in n-hexane.

2. Study on Reaction Temperature

Pentaerythritol does not react with $P_2O_5$ in toluene solvent at a temperature lower than 70° C. When the temperature increases to 90° C., pentaerythritol can undergo a phosphate esterification reaction. The reaction time is about 10 hours. When the temperature rises to 105° C., the reaction time can be reduced to 6 hours.

3. Effects of the Particle Size of Pentaerythritol

The reaction yield and purity can be increased when, prior to the reaction, pentaerythritol is ground in toluene in a ball mill.

4. Ball Mill Process

Based on the above studies 1~3, the key factors affecting the method of the present invention include: heating of the solvent, material with a fine particle size, and complete mixing in the reaction. Therefore, a ball mill is considered as a reactor to achieve a complete grinding, mixing and thermal insulation in the reaction. A suitable reaction time is 4–20 hours.

5. Formation of Phosphoric Acid in the Reaction

When 2 moles of pentaerythritol reacts with 1 mole of $P_2O_5$, 3 moles of water will be generated. When 3 moles of water reacts with 1 mole of $P_2O_5$, 2 moles of phosphoric acid will be generated. Therefore, in theory, when 1 mole of pentaerythritol reacts with 1 mole of $P_2O_5$, 1 mole of pentaerythritol phosphate alcohol and 1 mole of phosphoric acid will be generated. A suitable mole ratio of pentaerythritol to $P_2O_5$ is 2:1 to 1:1.

The chemical reagents used in the following example and control example are listed in the following:
Pentaerythritol:
    CAS. No. [363-72-4], $C_5H_{12}O_4$, MW=136
di-Phosphorus (V) Oxide (Phosphorus Pentoxide):
    CAS. No. [1314-56-3], $P_2O_5$, FW=141.94
Magnesium Chloride Anhydrous:
    CAS. No. [7786-30-3], $MgCl_2$, MW=95.21, 98%
Toluene:
    CAS. No. [108-88-3], $C_7H_8$, MW=92.14

The reaction formulas involved in the example and control example are listed in the following:
(1) Pentaerythritol ($C_5H_{12}O_4$) and ½ mole of $P_2O_5$ undergo the following reaction to form 1 mole of Pentaerythritol phosphate alcohol ($C_5H_9O_5P$)

$C_5H_{12}O_4$ + 1/2 $P_2O_5$ 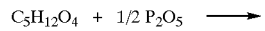

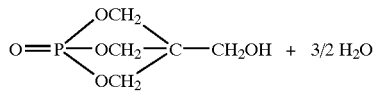

(2) Since $P_2O_5$ will be consumed by the ³⁄₂ moles of water simultaneously formed during the reaction, an excessive amount of $P_2O_5$ is needed in the reaction. Therefore, a small amount of $H_3PO_4$ will be also formed together with the product pentaerythritol phosphate alcohol.

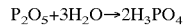

Since $P_2O_5$ is extremely hygroscopic, the feeding needs to use an enclosed feeding device for solid feed, and the reaction needs to take place in a nitrogen environment.

CONTROL EXAMPLE

Mechanical Agitation 0.1 mole of pentaerythritol was used in the synthesis steps as follows:

(A) 13.6 g (0.1 mol) of pentaerythritol and 0.2 g of anhydrous $MgCl_2$ (catalyst) were placed in a 500 ml three-necked round bottomed flask. Approximately 300 ml of toluene solvent was added into the flask. Nitrogen was introduced into the flask and the mixture was stirred and heated to 70° C.

(B) 8.5 g of $P_2O_5$ was weighed into a solid feeding device in a nitrogen box. The two ends of the feeding device were sealed and the feeding device was rapidly removed and loaded into the reaction device.

(C) $P_2O_5$ was slowly fed in batchwise into the toluene in the three-necked round bottomed flask in 30 minutes while stirring. The temperature was maintained at 50° C.

(D) Upon completion of the feeding of $P_2O_5$, the temperature was raised to 90° C. and the reaction took place for 10 hours.

(E) Upon completion of the reaction, before the temperature decreased, the viscous glue-like solid was removed and washed twice with 50 ml of methylene chloride, and dried at a reduced pressure. After cooling, the product was a light yellow solid. The product mixture contained about 32.5% of phosphoric acid, and the yield of pentaerythritol phosphate alcohol is about 47%.

EXAMPLE

Agitation by Ball Mill

A ball mill was used as a reactor. The grinding was taking place while the reaction was carrying out in order to disperse the reactants and achieve a complete reaction.

A one-liter ball mill bowl was used as a reaction container. Ceramic balls with a diameter of 2 cm were used. The basic reaction model was similar to the mechanical agitation process of Control Example.

(1) The amounts of the reactants were the same as in Control Example. 400 ml of toluene was pre-heated to 90~100° C. before use. After drying of the ball mill, the pre-heated solvent was added, and then pentaerythritol, $MgCl_2$ and $P_2O_5$, were sequentially added. Ceramic balls were then added. The ball mill was sealed and the rotation started. The reaction was carried out for 6 hours. The reaction liquid was poured out, and the solvent contained therein was removed under a reduced pressure. The obtained product mixture contained 79.2% of pentaerythritol phosphate alcohol and 20.8% of phosphoric acid. The yield of pentaerythritol phosphate alcohol is greater than 95%.

(2) Procedures similar to (1) in this example were repeated, except that the 400 ml toluene was used without pre-heating. The reaction time was about 10 hours to have the same level of yield as (1).

$^{31}$P-NMR was used to identify the main components in the products obtained by the mechanical agitation process of Control Example and the mechanochemical synthesis ball mill process of Examples, wherein DMSO $d_6$ was used as a solvent. The results indicate that the resonance at 0.4 ppm was phosphoric acid, -6.4 ppm was P on the bicyclo ring (pentaerythritol phosphate alcohol, as shown in Example 1 of EP 0 578 318 A1), -12 ppm was a pyrophosphoric acid product. Furthermore, the IR spectrums of the products obtained from the mechanical agitation process of Control Example and the ball mill process of Example were substantially the same and contained the following major characteristic absorption wavelength:
969 (strong broad): P—O—$CH_2$R Vibration
1164~1185 (strong): P=O-Vibration

What is claimed is:

1. A method for preparing pentaerythritol phosphate alcohol by a mechanochemical synthesis, which comprises ball milling a mixture including $P_2O_5$, pentaerythritol, an alkyl benzene having one or two C1–C5 alkyls, and a metal halide catalyst, in a ball mill reactor at a temperature of 70–150° C.

2. The method as claimed in claim 1, wherein said alkyl benzene is toluene, and said metal halide catalyst has a formula $MX_2$, wherein M is Mg, Zn or Al, and X is Cl or Br.

3. The method as claimed in claim 2, wherein said catalyst is $MgCl_2$.

4. The method as claimed in claim 1, wherein a molar ratio of said pentaerythritol to $P_2O_5$ in said mixture is 2:1 to 1:1.

5. The method as claimed in claim 1, wherein a weight ratio of said catalyst to pentaerythritol in said mixture is 1:99 to 5:95.

6. The method as claimed in claim 1, wherein said ball milling is carried out for 4–20 hours.

7. The method as claimed in claim 1, wherein said temperature is 90–105° C.

8. The method as claimed in claim 2, wherein said toluene is pre-heated to a temperature of 90–100° C. prior to being added to said ball mill; and said ball milling is carried out in the ball mill without heating.

* * * * *